United States Patent
Suzuki et al.

(10) Patent No.: US 6,255,313 B1
(45) Date of Patent: Jul. 3, 2001

(54) SUSTAINED RELEASE HAIR GROWTH COMPOSITION

(75) Inventors: Kenichi Suzuki; Kouji Imamura; Susumu Morioka; Shigeo Tanaka, all of Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/341,191

(22) PCT Filed: Jan. 22, 1998

(86) PCT No.: PCT/JP98/00227

§ 371 Date: Jul. 6, 1999

§ 102(e) Date: Jul. 6, 1999

(87) PCT Pub. No.: WO98/32417

PCT Pub. Date: Jul. 30, 1998

(30) Foreign Application Priority Data

Jan. 23, 1997 (JP) .................................................. 9-010531

(51) Int. Cl.$^7$ ....................... A61K 31/505; A61K 31/045
(52) U.S. Cl. ............................ 514/272; 514/738; 514/880

(58) Field of Search .................................... 514/272, 738, 514/880

(56) References Cited

U.S. PATENT DOCUMENTS 4,139,619  2/1979  Chidsey et al. ........................ 424/45

FOREIGN PATENT DOCUMENTS

| 572167 | 5/1993 | (EP) . |
|---|---|---|
| 64-68310 | 3/1989 | (JP) . |
| 1132510 | 5/1989 | (JP) . |
| 262818 | 3/1990 | (JP) . |
| 640846 | 2/1994 | (JP) . |
| 8277209 | 10/1996 | (JP) . |

Primary Examiner—Rebecca Cook
(74) Attorney, Agent, or Firm—Lorusso & Loud

(57) ABSTRACT

A sustained hair growth preparation comprising minoxidil and dipropylene glycol makes it possible to retain the absorbed minoxidil in the dermis and to increase the concentration of the minoxidil around the hair bulbs which are the hair growing sites, thereby making it possible to give a sufficient hair growth effect.

10 Claims, No Drawings

SUSTAINED RELEASE HAIR GROWTH COMPOSITION

This is a 317 of PCT/JP98/00227 filed Jan. 22, 1998.

TECHNICAL FIELD

The present invention relates to a sustained release hair growth preparation wherein minoxidil is an effective component.

BACKGROUND ART

Minoxidil is called 6-(1-piperidinyl)-2,4-pyrimidinediamine-3-oxide by the chemical name, and described to be adaptable as a hair growth agent in U.S. Pat. No. 4,139,619.

In the past, minoxidil-containing hair growth preparations needed to be applied several times per day, therefore such application is very troublesome and tends to be forgotten, as a result, there are instances where an insufficient hair growth effect is seen.

DISCLOSURE OF THE INVENTION

The present inventors have variously researched under the conception that, when minoxidil is used as a hair growth agent, it will be possible to provide a hair growth preparation having a sufficient hair growth effect with even only a once-per-day application, by allowing to retain the percutaneously absorbed minoxidil in the dermis, and thus by raising the concentration of minoxidil over a long period around the hair bulbs which are the hair growing sites.

As a result, the combination of the minoxidil-containing hair growth preparation with dipropylene glycol has been found to maintain minoxidil in the dermis for a long period of time, thus the present invention has been accomplished.

Accordingly, the present invention is directed to a sustained release hair growth preparation which comprises minoxidil and dipropylene glycol.

In the present invention, the amount of minoxidil is from 0.1 to 10% by weight, which is an ordinary amount of minoxidil used as an effective component of hair growth preparations.

In the present invention, the amount of dipropylene glycol is preferably from 5 to 40% by weight based on the total weight of the preparation. When the amount of dipropylene glycol is less than 5% by weight, the retention effect of minoxidil in the dermis is insufficient, and when the amount is more than 40% by weight, the resulting preparation gives a bad feeling in use.

Furthermore, the preparation of the present invention is preferably adjusted to a pH of 4 to 9, and especially pH 5 to 8, when diluted 20-fold with purified water. When the pH of the preparation is out of the above-mentioned range, the retention effect of minoxidil in the dermis may decrease, and skin irritation may occur.

In the hair growth preparation of the present invention, a further combination of 1,3-butylene glycol or propylene glycol with the preparation can shorten the time for reaching the maximum concentration (Tmax) of minoxidil in the dermis. Furthermore, the retention time of minoxidil in the dermis can be further prolonged by the combination of the preparation with a polar solvent selected from the group consisting of 2-hexyl-1-decanol, isooctadecanol, glycerol dicaprate, glycerol dicaprylate, glycerol monoisostearate and propylene glycol monoisostearate. Accordingly, such combination of these substances makes it possible to control the dose and the number of application times of the hair growth preparation.

In the present invention, when 1,3-butylene glycol or propylene glycol is contained therein, its amount is preferably from 0.1 to 10 parts by weight, and especially from 0.1 to 5 parts by weight per 1 part by weight of dipropylene glycol, in view of the Tmax-shortening effect and the retention effect of minoxidil in the dermis. Furthermore, when the preparation is combined with the polar solvent selected from the group consisting of 2-hexyl-1-decanol, isooctadecanol, glycerol dicaprate, glycerol dicaprylate, glycerol monoisostearate and propylene glycol monoisostearate, the amount of the polar solvent is preferably from 0.005 to 5 parts by weight, and especially from 0.01 to 2 parts by weight per 1 part by weight of dipropylene glycol, in view of the extension effect on the retention period of minoxidil in the dermis and the maximum concentration of minoxidil in the dermis.

According to the present invention, components used for ordinary hair growth preparations can be contained therein, for example, fillers, vasidilators (carpronium chloride, benzyl nicotinate, swertia herb extract, panax ginseng extract, vitamin E acetate, capsicum tincture, etc.), antihistamines (diphenhydramine hydrochloride, isothipendyl hydrochloride, etc.), anti-inflammatory agents (glycyrrhetic acid, guaiazulene, etc.), keratolytics (urea, salicylic acid, etc.), antimicrobial agents (chlorhexidine gluconate, isopropyl methyl phenol, quaternary ammonium salts, hinokitiol, piroctone olamine, etc.), humectants (sodium hyaluronate, chondroitin sulfuric acid, etc.), extracts of animals and plants (Taxus cuspidata, Paeonia suffruticosa, Glycyrrhisa uralensis, Hypericum erectum, aconite root, Eriobotrya japonica, Artemisia capillaris, Symphytum officinale, Angelica keiskei, Crocus sativus, Gardeniac Fructus, Posmarinus officinalis, Salvia officinalis, saussurea root, Aristolochia debilis, Lupuli strobilus, placenta, etc.), vitamins (retinol acetate, pyridoxine hydrochloride, ascorbic acid, thiamin nitrate, cyanocobalamin, biotin, etc.), water, lower alcohols (methanol, ethanol, denatured ethanol, isopropyl alcohol, etc.), anti-oxidants (dibutylhydroxytoluene, sodium pyrosulfite, tocopherol, disodium edetate, ascorbic acid, isopropyl gallate, etc.), solubilizers (diisopropyl adipate, isopropyl myristate, polyethylene glycol, medium chain fatty acid triglyceride, fatty acid esters, vegetable oils, animal oils, polyhydric alcohol fatty acid ester, alkyl glyceryl ether, hydrocarbons, lactic acid, sodium hydroxide, etc.), metabolic activators (panthenol, etc.), surface active agents (sorbitan fatty acid ester, glycerol fatty acid ester, polyglycerol fatty acid ester, propylene glycol fatty acid ester, polyoxyethylene sorbitan fatty acid ester, polyoxyethylene sorbitol fatty acid ester, polyoxyethylene glycerol fatty acid ester, polyethylene glycol fatty acid ester, polyoxyethylene alkyl ether, polyoxyethylene polyoxypropylene alkyl ether, polyoxyethylene alkyl phenyl ether, polyoxyethylene hydrogenated castor oil, polyoxyethylene castor oil, polyoxyethylene beeswax derivatives, polyoxyethylene lanolin derivatives, polyoxyethylene alkyl amide, polyoxyethylene alkyl amine, lecithin derivatives, high molecular emulsifiers, etc.), emulsifying stabilizers (higher alcohol, etc.), gelling agents (water-soluble high molecular compounds, etc.), thickeners, perfumes, refrigerants (menthol, mentha oil, camphor, etc.) or dyes. When water or a lower alcohol is contained herein, water content is preferably from 0.5 to 30% by weight based on the total weight of the preparation, and when ethyl alcohol or isopropyl alcohol is contained as the lower alcohol, its amount is preferably from 50 to 90% by weight based on the total weight of the preparation.

The hair growth preparation of the present invention can be produced by an ordinary method in the form of an external preparation such as creams, ointments, aerosols, lotions or tonics. In addition, the sustained release hair growth preparation of the present invention can be used by applying a suitable amount thereof percutaneously once per one to several days. Applied in this manner, the composition of the present invention is effective in treating alopecia and baldness.

BEST MODE FOR CARRYING OUT THE INVENTION

The present invention is illustrated in more detail by the following example and experiments.

EXAMPLE

According to the formulations shown in Table 1, minoxidil and dipropylene glycol were combined with other components, made up to the total volume of 100 ml with anhydrous ethanol and purified water, and dissolved with stirring, thereby there were obtained external hair growth preparations of lotion type of Examples 1 to 13 and Comparative Examples 1 and 2.

TABLE 1

Ex. = Example, Cmp. = Comparative Example, Unit: gram

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| minoxidil | 2 | 2 | 2 | 2 | 2 | 2 | 2 | 2 |
| dipropylene glycol | 20 | 15 | 15 | 15 | 20 | 20 | 20 | 20 |
| 1,3-butylene glycol |  | 5 |  | 2.5 |  |  |  |  |
| propylene glycol |  |  | 5 | 2.5 |  |  |  |  |
| glycerol monoisostearate |  |  |  |  | 2 |  |  |  |
| propylene glycol monoisostearate |  |  |  |  |  | 2 |  |  |
| glycerol dicaprate |  |  |  |  |  |  | 2 |  |
| isostearyl alcohol |  |  |  |  |  |  |  | 2 |
| hexadecyl alcohol |  |  |  |  |  |  |  |  |
| anhydrous ethanol | | | | | 60 ml | | | |
| purified water | | | | | Total 100 ml | | | |
| pH when diluted to 20-fold | 7.4 | 7.2 | 7.2 | 7.1 | 7.0 | 7.0 | 7.0 | 7.2 |

|  | Ex. 9 | Ex. 10 | Ex. 11 | Ex. 12 | Ex. 13 | Cmp. 1 | Cmp. 2 |
|---|---|---|---|---|---|---|---|
| minoxidil | 2 | 2 | 2 | 2 | 2 | 2 | 2 |
| dipropylene glycol | 20 | 30 | 40 | 3 | 5 |  |  |
| 1,3-butylene glycol |  |  |  |  |  |  |  |
| propylene glycol |  |  |  |  |  |  |  |
| glycerol monoisostearate |  |  |  |  |  |  |  |
| propylene glycol monoisostearate |  |  |  |  |  |  |  |
| glycerol dicaprate |  |  |  |  |  | 20 |  |
| isostearyl alcohol |  |  |  |  |  |  |  |
| hexadecyl alcohol | 2 |  |  |  |  |  |  |
| anhydrous ethanol |  | 60 ml |  | Total 100 ml |  | 60 ml |  |
| purified water |  | Total 100 ml | — |  | Total 100 ml |  |  |
| pH when diluted to 20-fold | 7.1 | 7.2 | 7.3 | 7.2 | 7.1 | 7.5 | 7.4 |

Experiment 1. Concentration of Minoxidil in Blood and Content of minoxidil in Dermis Male Wister rats, 7 weeks old, whose abdominal hairs were shaved, were fixed on the supine under ether anesthesia, and 40 $\mu$l of each lotion of Table 1 was applied on the defined area (2×4 cm) of the abdomen. After the defined time (1, 2, 4, 6, 8, 12 and 24 hours), blood was collected from the thoracic vein, the concentration of minoxidil in blood was measured by a liquid scintillation counter, and the change of the concentration in blood is shown in Table 2. Furthermore, in order to measure the content of minoxidil in the dermis, rats were sacrificed by decapitation, the epidermis applied with the lotion was washed with ethanol, the skin was removed, and the whole epidermis was tightly strapped with transparent adhesive tape, wrapped in plastic food-protective wrap and soaked in a hot water bath at 60° C. for 60 seconds. After allowing to stand for cooling, the tape was peeled to remove the residual drug and the epidermal layer from the skin, the weight of the residual dermis and the content of minoxidil in the dermis were measured, and the content of minoxidil per 1 g of the dermis was determined. The change of the concentration in the dermis was shown in Table 3.

TABLE 2

Unit: ng/ml

|  | 0 h | 1 h | 2 h | 4 h | 6 h | 8 h | 12 h | 24 h |
|---|---|---|---|---|---|---|---|---|
| Ex. 1 | 0.00 | 1.00 | 2.00 | 3.00 | 2.67 | 2.00 | 1.00 | 0.00 |
| Ex. 2 | 0.00 | 1.33 | 2.33 | 3.33 | 3.00 | 2.33 | 1.00 | 0.00 |
| Ex. 3 | 0.00 | 1.67 | 2.67 | 3.33 | 3.00 | 2.00 | 1.00 | 0.00 |
| Ex. 4 | 0.00 | 1.33 | 2.33 | 3.00 | 2.33 | 1.67 | 0.67 | 0.00 |
| Ex. 5 | 0.00 | 0.33 | 1.33 | 2.67 | 1.67 | 1.33 | 0.67 | 0.00 |
| Ex. 6 | 0.00 | 1.00 | 1.67 | 2.33 | 1.33 | 0.33 | 0.00 | 0.00 |
| Ex. 7 | 0.00 | 1.00 | 1.67 | 3.33 | 2.33 | 1.00 | 0.33 | 0.00 |
| Ex. 8 | 0.00 | 1.67 | 2.33 | 3.00 | 2.67 | 1.33 | 1.00 | 0.00 |
| Ex. 9 | 0.00 | 2.33 | 3.00 | 2.67 | 2.00 | 1.33 | 0.67 | 0.00 |

TABLE 2-continued

Unit: ng/ml

|  | 0 h | 1 h | 2 h | 4 h | 6 h | 8 h | 12 h | 24 h |
|---|---|---|---|---|---|---|---|---|
| Ex. 10 | 0.00 | 1.10 | 1.95 | 2.50 | 3.30 | 2.71 | 2.00 | 0.00 |
| Ex. 11 | 0.00 | 1.20 | 1.60 | 2.40 | 3.00 | 3.30 | 2.40 | 0.00 |
| Ex. 12 | 0.00 | 3.50 | 6.31 | 3.24 | 1.82 | 0.78 | 0.55 | 0.00 |
| Ex. 13 | 0.00 | 2.10 | 2.78 | 3.20 | 2.21 | 1.35 | 0.78 | 0.00 |
| Cmp. 1 | 0.00 | 8.00 | 2.25 | 0.68 | 0.23 | 0.22 | 0.15 | 0.05 |
| Cmp. 2 | 0.00 | 10.00 | 7.00 | 3.00 | 1.50 | 0.60 | 0.25 | 0.00 |

TABLE 3

| | μg/1 g of skin | | | | | | | |
|---|---|---|---|---|---|---|---|---|
| | 0 h | 1 h | 2 h | 4 h | 6 h | 8 h | 12 h | 24 h |
| Ex. 1 | 0 | 2 | 4 | 8 | 12 | 15 | 18 | 8 |
| Ex. 2 | 0 | 2 | 5 | 7 | 9 | 12 | 8 | 3 |
| Ex. 3 | 0 | 5 | 8 | 14 | 9 | 7 | 4 | 1 |
| Ex. 4 | 0 | 3 | 5 | 9 | 13 | 8 | 6 | 2 |
| Ex. 5 | 0 | 0 | 2 | 3 | 5 | 8 | 9 | 6 |
| Ex. 6 | 0 | 0 | 4 | 5 | 8 | 10 | 12 | 8 |
| Ex. 7 | 0 | 0 | 3 | 5 | 7 | 9 | 11 | 7 |
| Ex. 8 | 0 | 1 | 2 | 4 | 6 | 8 | 10 | 5 |
| Ex. 9 | 0 | 2 | 3 | 5 | 7 | 9 | 11 | 6 |
| Ex. 10 | 0 | 3 | 4 | 9 | 14 | 17 | 21 | 11 |
| Ex. 11 | 0 | 5 | 7 | 10 | 15 | 18 | 27 | 16 |
| Ex. 12 | 0 | 3 | 6 | 8 | 4 | 2 | 0 | 0 |
| Ex. 13 | 0 | 1 | 3 | 5 | 6 | 8 | 7 | 1 |
| Cmp. 1 | 0 | 6 | 2 | 1 | 1 | 0 | 0 | 0 |
| Cmp. 2 | 0 | 4 | 9 | 3 | 2 | 1 | 0 | 0 |

As apparent from the results in Tables 2 and 3, the sustained release hair growth preparation of the present invention is recognized to be more effective in lowering the diffusion of minoxidil into blood, to the contrary, in raising the concentration in the dermis for a longer period than any comparative example. Experiment 2. Hair Generation Test Ten male C3H mice, 7 weeks old, were used for each group, and dorsal hairs in the area range of 2×3 cm of animals of each group were shaved by a pair of hair clippers in order to serve the test. Animals of different group were assigned to each sample in Table 1, 0.2 ml of which was applied to the shaved area once a day.

The animals used for the test had black body-hairs, while the color of skin around the shaved area was brown, accordingly, the tone of color was changed from brown to black with hair growth, thereby the degree of black hair was evaluated macroscopically by the following six grades: 0: no hair generation is observed, 1: hair generation is observed, 2: terminal hairs grow, 3: terminal hairs grow on about 50% of the normal, 4: terminal hairs grow on about 70% of the normal, and 6: terminal hairs grow on about 100% of the normal. Results are shown in Table 4.

TABLE 4

| | Microscopical evaluation | |
|---|---|---|
| Test sample | after 10 days | after 20 days |
| Example 1 | 3 | 5 |
| Example 2 | 2 | 5 |
| Example 3 | 2 | 5 |
| Example 4 | 2 | 5 |
| Example 5 | 2 | 5 |
| Example 6 | 2 | 5 |
| Example 7 | 2 | 5 |
| Example 8 | 2 | 5 |
| Example 9 | 2 | 5 |
| Example 10 | 3 | 5 |
| Example 11 | 3 | 5 |
| Example 12 | 1 | 5 |
| Example 13 | 2 | 5 |
| Comparative Example 1 | 1 | 3 |
| Comparative Example 2 | 1 | 4 |

As apparent from Table 4, it was confirmed that the preparation of the present invention causes a higher degree of hair generation when compared with any comparative example.

INDUSTRIAL APPLICABILITY

The present invention makes it possible to retain minoxidil in the dermis, and thereby to provide a sustained release hair growth preparation which is effective with even a few application times.

What is claimed is:

1. A sustained release hair growth composition which comprises minoxidil and 5 to 40% by weight of dipropylene glycol based on the composition.

2. The sustained release hair growth composition according to claim 1 which has a pH of from 4 to 9, when diluted 20-fold with purified water.

3. The sustained release hair growth composition according to claim 1 wherein the amount of minoxidil is from 0.1 to 10% by weight based on the total weight of the composition.

4. The sustained release hair growth composition according claim 1 which further comprises at least one polar solvent selected from the group consisting of 2-hexyl-1-decanol, isooctadecanol, glycerol dicaprate, glycerol dicaprylate, glycerol monoisostearate and propylene glycol monoisostearate.

5. The sustained release hair growth composition according to claim 1 which further comprises at least one polar solvent selected from the group consisting of 2-hexyl-1-decanol, isooctadecanol, glycerol dicaprate, glycerol dicaprylate, glycerol monoisostearate and propylene glycol monoisostearate in the amount of from 0.005 to 5 parts by weight per 1 part by weight of dipropylene glycol.

6. The sustained release hair growth composition according to claim 1 which further comprises at least one polyhydric alcohol selected from the group consisting of 1,3-butylene glycol and propylene glycol.

7. The sustained release hair growth composition according to claim 1 which comprises at least one polyhydric alcohol selected from the group consisting of 1,3-butylene glycol and propylene glycol in the amount of from 0.1 to 10% by weight based on the composition.

8. The sustained release hair growth composition according to claim 1 which comprises at least one polyhydric alcohol selected from the group consisting of 1,3-butylene glycol and propylene glycol in the amount of from 0.1 to 10 parts by weight per 1 part by weight of dipropylene glycol.

9. A method for treating baldness which comprises applying the sustained release hair growth composition according to claim 1.

10. A method for treating alopecia which comprises applying the sustained release hair growth composition according to claim 1.

* * * * *

UNITED STATES PATENT AND TRADEMARK OFFICE
CERTIFICATE OF CORRECTION

PATENT NO. : 6,255,313 B1
DATED : July 3, 2001
INVENTOR(S) : Suzuki et al

It is certified that error appears in the above-identified patent and that said Letters Patent is hereby corrected as shown below:

Column 1,
Line 39, "and dipropylene glycol." should read -- 5 to 40% by weight of dipropylene glycol based on the preparation --.

Signed and Sealed this

Fourth Day of June, 2002

Attest:

JAMES E. ROGAN
Attesting Officer    Director of the United States Patent and Trademark Office